US00PP09577P

United States Patent [19]

Eilers

[11] Patent Number: Plant 9,577

[45] Date of Patent: Jun. 11, 1996

[54] *BERBERIS THUNBERGII* CV. 'MONLERS'

[75] Inventor: Henry H. Eilers, Litchfield, Ill.

[73] Assignee: Monrovia Nursery Company, Azusa, Calif.

[21] Appl. No.: 419,602

[22] Filed: Apr. 10, 1995

[51] Int. Cl.[6] ..... A01H 5/00

[52] U.S. Cl. ..... Plt./58

[58] Field of Search ..... Plt./58

[56] References Cited

U.S. PATENT DOCUMENTS

P.P. 8,215 4/1993 Moretti ..... Plt./58

*Primary Examiner*—James R. Feyrer

[57] ABSTRACT

A new and distinct selection of Golden Barberry shrub which shall be referred to hereinafter a *Berberis thunbergii* cultivar Monlers. *Berberis thunbergii* cultivar Monlers differs distinctively from other *Berberis thunbergii* plants by its unique combination of a low, dense symmetrical globe habit and dwarf size and golden yellow foliage which does not appear to scorch in full sun.

1 Drawing Sheet

BACKGROUND OF THE NEW PLANT

This invention relates to a new and distinct selection of *Berberis thunbergii,* a member of the Berberidaceae or Barberry family. *Berberis thunbergii* cultivar Monlers was discovered in a group of seedlings around the year 1977. The seedlings were a product of an uncontrolled cross but believed to be *Berberis thunbergii* 'Aurea' crossed with *Berberis thunbergii* 'Kobold'. This seedling was selected from 50 to 100 other seedlings as it exhibited a slow growing compact habit, golden yellow foliage with an orange cast and red orange fall color. My new plant has been asexually reproduced by cuttings since the discovery at H E Nursery, R.R. 3, Box 4, Litchfield, Ill., 62056 and later at Monrovia Nursery Company, 13455 S.E. Lafayette Hwy, Dayton, Org. The original seedlings displayed extreme variability, therefore the distinct phenotypic characteristics of my new selection that sets this plant apart from other *Berberis thunbergii* plants would likely be lost through sexual reproduction. Because the plant of this disclosure 'Monlers' is believed to be highly heterozygous, as indicated by the variation expressed by its siblings, it is believed that attempts to reproduce it through sexual reproduction, by planting seeds, would be futile. However, faithful clones of this plant may be propagated through multiplication by the rooting of cuttings as noted above. Without isolation of and preservation of this plant, it would have been lost to mankind.

SUMMARY OF INVENTION

*Berberis thunbergii* cv. Monlers is unusual in the dwarf growth habit. Normal *Berberis thunbergii* cv. Aurea is a rounded shrub 3–4' (about 100–130 cm) in height and width. My new selection after 10 years is 15" tall and 15' wide or about 38 cm in both height and width. A recent selection *Berberis thunbergii* 'Bogozam' plant patent 8215 lists size at 18" tall by 36" wide (near 48 cm high by 76 cm wide.) In comparison growing at Monrovia Nursery in Dayton, Oreg. since 1990 cultivar Bogozam exhibits a low, full growth habit with long branch shoots arching out and not as dense overall. The internodes of 'Monlers' range between about ½–¾ inch (1–2 cm), while those of 'Bogozam' are closer to ¾–1 inch. Comparison 6 year specimens of 'Monlers' measure 12–15 inches (30–38 cm) while those of 'Bogozam' range between 15–18 inches, (38–46 cm). The spines of my plant are 3 in number with the center spine being near ⅜ inch (1 cm) long and outer spines being about ⅛ inch (3–4 mm). 'Bogozam' also has 3 spines, but they measure ¼ inch (about 6–7 mm) for the center spine, with the outer spines being ⅜ (1 cm) long. Further, vegetative buds of 'Monlers' are formed in clusters, and are about ⅛ inch (4 mm) in length, while those of 'Bogozam' are borne singly or fewer in number and are larger; ranging from ⅛–⅜ inch or about 4–10 mm. Whereas, my selection is a low, dense, symmetrical globe with even growth and more tight growing foliage. Cultivar Monlers exhibits a golden yellow foliage with lime green undertones in shade. Cultivar Aurea the standard exhibits a light yellow foliage color. Cultivar Bogozam has foliage color similar to cultivar Aurea. In comparison growing tests cultivar Monlers does not foliage scorch in full sun conditions in containers. Cultivars Aurea and Bogozam will scorch in full sun in containers. The plant of this disclosure is characterized by being exceedingly compact, of uncommonly high canopy density, conspicuously attractive coloration, and has advantageously slow growth. The tight upward habit and fine textural appearance affords utilization as a colorfully contrasting and low maintenance appointment for the landscape gardener for use as a specimen plant in flower bed decoration, for foundation planting, as well as in mass plantings.

BRIEF DESCRIPTION OF DRAWINGS

The upper photograph is a foliage close-up of cultivar Monlers on the left and cultivar Aurea. My selection exhibits a more golden color mixed with undertones of green and less yellow foliage. The internodal length is closer and foliage slightly smaller.

The lower photograph compares the growth habits of cultivar Monlers on the left and cultivar Aurea on the right. My selection displays a tight dense habit.

BOTANICAL DESCRIPTION

Below is detailed description of my new selection of *Berberis thunbergii* cv. Monlers, the color terminology is from the British Horticultural Color Charts.

Overall size and habit: Deciduous shrub. After 10 years the plant has achieved a height and spread of 15 inches (37.5 cm).

Flowers: Yellow in Spring, not significant.

Leaf:

*Arrangement.*—Alternate.

*Size.*—Lower shaded leaves 2–3 cm long; 1–1.2 cm wide upper new foliage exposed to sun 1.0–1.5 cm long; 0.5–0.8 cm wide Shape: Spatulate, long petiole.

Color: New growth.

*Tips.*—Combine Lettuce Green 861/3 and Uranium Green 63/1.

*Lower shady area.*—Lettuce Green 861/2 to 861/3.

*Margins.*—of freshly emerged leaves Poppy Red 16/1.

Mature growth: Combinations of Uranium Green 63/1, and Sulphur Yellow 1/11 and Buttercup Yellow 5/1 (the Buttercup Yellow gives an overall orange cast).

Spines: 3-parted, central spine 3–5 mm color of tips: Poppy Red 16/1.

Fruit: Bright red in Fall 1 cm long ×5 mm wide.

General Observations: The red orange fall color has not been systematically recorded, but may vary with progressive changes in environmental conditions in the location of culture.

I claim:

1. A new and distinct variety of Berberis plant as substantially shown and described herein, that is characterized particularly as a novelty by the unique combination of a low, dense symmetrical globe habit and dwarf size and golden yellow foliage which does not appear to scorch in full sun.

* * * * *

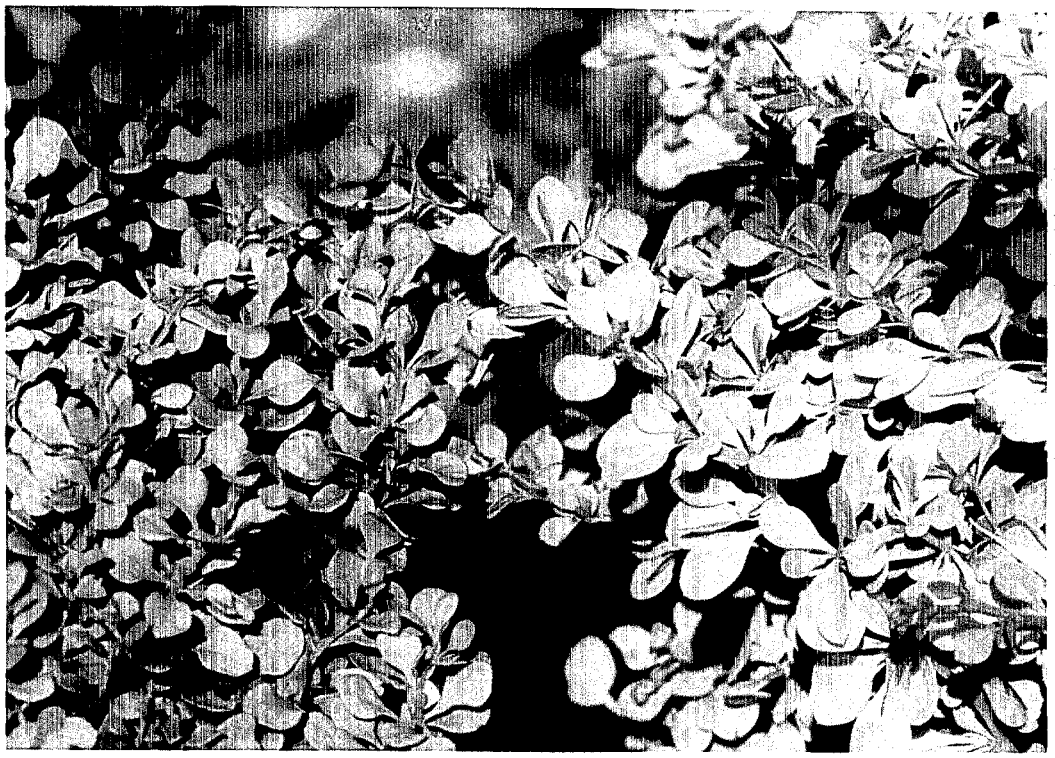
PRIOR ART
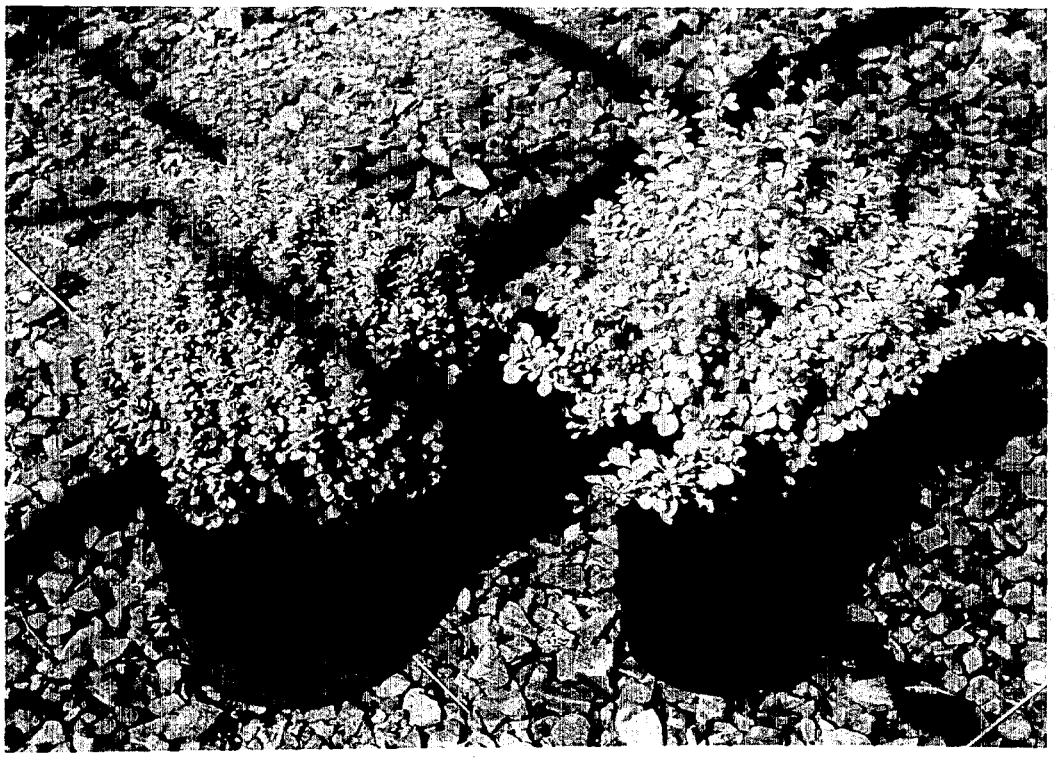
PRIOR ART